United States Patent
Shi

(10) Patent No.: US 8,026,373 B1
(45) Date of Patent: Sep. 27, 2011

(54) 1,2,3-TRIAZOLE BOUND BORANE COMPOUNDS, SYNTHESIS OF, AND USE IN REDUCTION REACTIONS

(75) Inventor: Xiaodong Shi, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 12/798,299

(22) Filed: Apr. 1, 2010

(51) Int. Cl.
*C07D 403/00* (2006.01)
(52) U.S. Cl. ...................................................... 548/255
(58) Field of Classification Search .................. None
See application file for complete search history.

(56) References Cited

OTHER PUBLICATIONS

Oziminski et al., caplus an 2003:429883.*
Brock et al., caplus an 1991:102144.*
U.S. Appl. No. 12/228,924, Xiaodong Shi.
U.S. Appl. No. 12/584,801, Xiaodong Shi.
Liao, W.; Chen, Y.; Duan, H.; Liu, Y.; Petersen, J. L.; Shi, X. "1,2,3-Triazole-boranes: stable and efficient reagents for ketone and aldehyde reductive amination in organic solvents or in water" Chem. Commun. 2009, 6436-6438.

* cited by examiner

Primary Examiner — Sun Jae Loewe
(74) Attorney, Agent, or Firm — William Aylur

(57) ABSTRACT

A 1,2,3-triazole coordinated borane such as

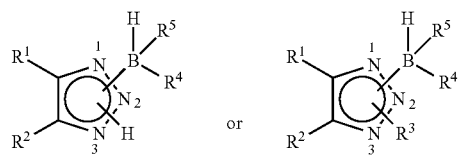

where the B and the $R^3$ groups can be on any of the three N positions and $R^1$, $R^2$, $R^3$, $R^4$, and $R^5$ can be one or more of H, any alkyl, aryl, or substituted alkyl or aryl groups and the position of the final products are the combination of any N position; i.e. $N^1$—$R^3$—$N^3$—BH etc. The triazole-borane compounds can be synthesized in a single-step from simple organic molecules under mild reactions. The 1,2,3-triazole coordinated borane can be synthesized by use of about a 1 to 1 equivalent of the benzole-triazole and the $BR_3$ can be added together without solution or dissolved in an organic solvent (between about 5 M to about 0.001 M for each reactant). The solution can be stirred for about 1 to about 5 hours at an effective temperature to yield the triazole-borane. These compounds can be used as an effective reductant in a reduction reaction for one or more of the groups aldehyde, ketone, imine, and reductive coupling between aldehyde/ketone with amine (both primary and secondary) in a wide range of media.

1 Claim, No Drawings

1,2,3-TRIAZOLE BOUND BORANE COMPOUNDS, SYNTHESIS OF, AND USE IN REDUCTION REACTIONS

CROSS-REFERENCE TO RELATED APPLICATIONS

REFERENCE TO SEQUENCE LISTING, A TABLE, OR A COMPUTER PROGRAM LISTING COMPACT DISC APPENDIX

Not Applicable

DETAILED DESCRIPTION OF THE INVENTION

A first embodiment is a 1,2,3-triazole coordinated borane such as

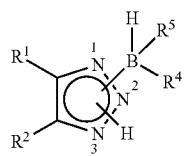

where B can be attached to $N^1$, $N^2$, or $N^3$ and $R^1$, $R^2$, $R^3$, $R^4$, and $R^5$ can be one or more of H, any alkyl, aryl, or substituted alkyl or aryl groups and the position of the final products are the combination of any N position; i.e. $N^1$—$R^3$—$N^3$—BH etc. Alternatively the triazole could be

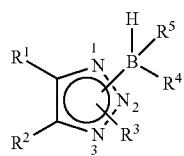

where $R^3$ can be attached to $N^1$, $N^2$, or $N^3$ and B can be attached to either of the other two remaining Ns and $R^1$, $R^2$, $R^3$, $R^4$, and $R^5$ can be one or more of H, any alkyl, aryl, or substituted alkyl or aryl groups and the position of the final products are the combination of any N position; i.e. $N^1$—$R^3$—$N^3$—BH etc.

The triazole-borane compounds can be synthesized in a single-step from simple organic molecules under mild reactions. The triazoles can be either alkyl or aryl substituted and N-substituted groups can also be either alkyl or aryl. The borane also can be a large different varity; from $BH_3$, $BHR_2$ or $BH_2R$ where R could be any combination of alkyne or aryl groups even with different substitute groups on the different Rs.

Example of Preparation of Triazole Boranes:

A) Preparation of triazole boranes

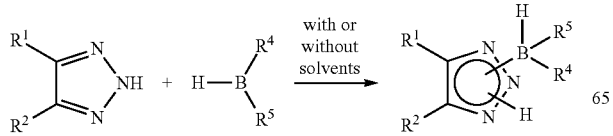

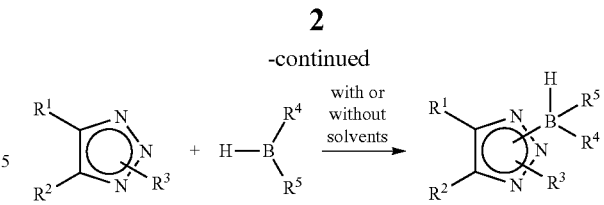

$R^1$, $R^2$, $R^3$, $R^4$, $R^5$ = any alkyl, aryl or substituted alkyl, aryl groups
position of the final products are the combination of any N position,
ie: N-1-$R^3$-$N^3$-BH etc
Solvents can be any organic solvents or water, including DCM, CH3CH, DMSO, DMF, THF, H2O, MeOH, EtOH, i-PrOH etc About a 1 to 1 equivalent of the benzole-triazole and the $BR_3$ can be added together without solution or dissolved in an organic solvent (between about 5 M to about 0.001 M for each reactant). The solution can be stirred for about 1 to about 5 hours at an effective temperature to yield the triazole-borane.

1.0 mol of methyl-benzole-triazole can be dissolved in THF (concentration between 5 M to 0.01 mol). The resulting solution can be added with 1.0 mol of $BH_3$ solution (either in THF of Hexcan or Pentane or other organic solvent, concentration from 0.1 M to 3.0 M). The solution was stirred for 1 to 5 hours and triazole-borane will be formed in near quantitive yields.

The 1,2,3-triazole-borane complexes are stable solid and X-ray crystal structure has been observed. These compounds can be used as an effective reductant in a reduction reaction for one or more of the groups aldehyde, ketone, imine, and reductive coupling between aldehyde/ketone with amine (both primary and secondary) in a wide range of media. The media can range from organic solvent to pure water such as MeOH, EtOH, i-PrOH, $H_2O$, DMSO, THF, DMF, DCM, $CH_3CN$ and others with or without additives. The reduction can be effective for aldehydes, ketones, and imines with any different substituted groups and alternatives. The reaction can be effective in a large temperature range from about $-70°$ C. to about $200°$ C. Additionally these compounds can effectively cause the reductive coupling between carbonyl foundation groups and amines (both primary and secondary amines) including effective condensation for simple sugar-amines and amino acid derivative-carbonyl condensation.

Examples of Reduction:
Reduction of Carbonyl Compounds and Imine

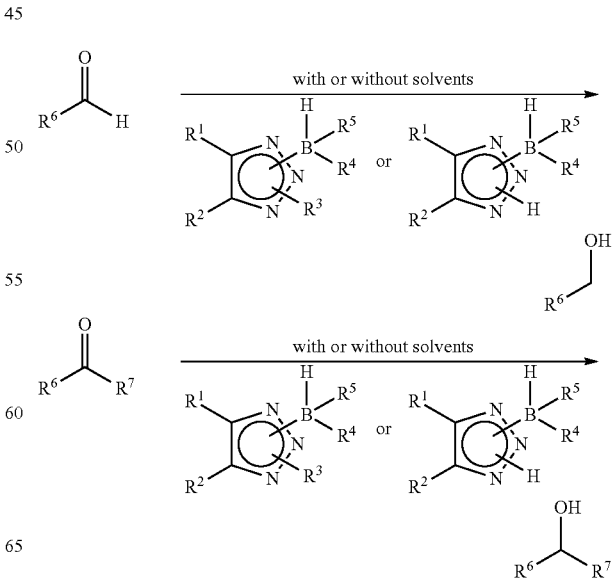

-continued

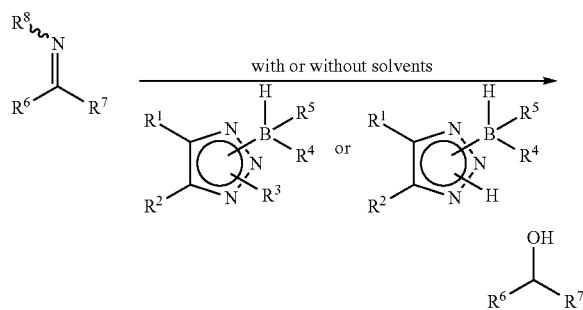

$R^1, R^2, R^3, R^4, R^5, R^6, R^7, R^8$ = any alkyl, aryl or substituted alkyl, aryl groups
position of the final products are the combination of any N position,
ie: N-1-$R^3$-$N^3$-BH etc Solvents can be any organic solvents or water, including DCM, CH3CH, DMSO, DMF, THF, H2O, MeOH, EtOH, i-PrOH etc Reductive Coupling:

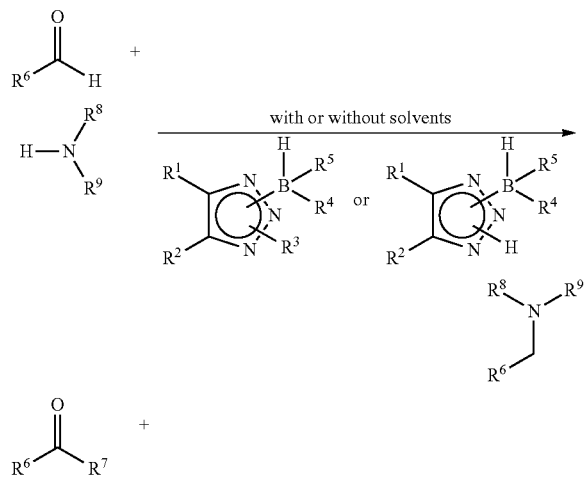

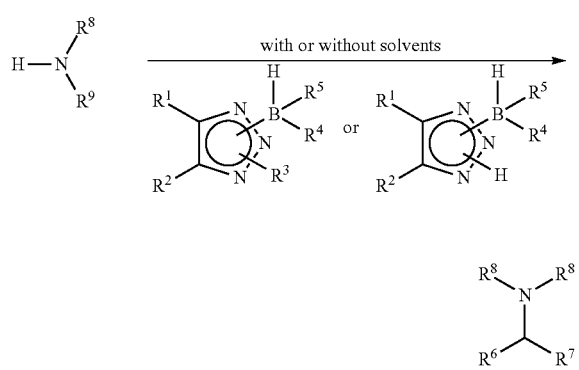

$R^1, R^2, R^3, R^4, R^5, R^6, R^7, R^8, R^9$ = any alkyl, aryl or substituted alkyl, aryl groups
position of the final products are the combination of any N position,
ie: N-1-$R^3$-$N^3$-BH etc Solvents can be any organic solvents or water, including DCM, CH3CH, DMSO, DMF, THF, H2O, MeOH, EtOH, i-PrOH etc Examples of Reduction Using 1,2,3-Triazole Borane Compounds:

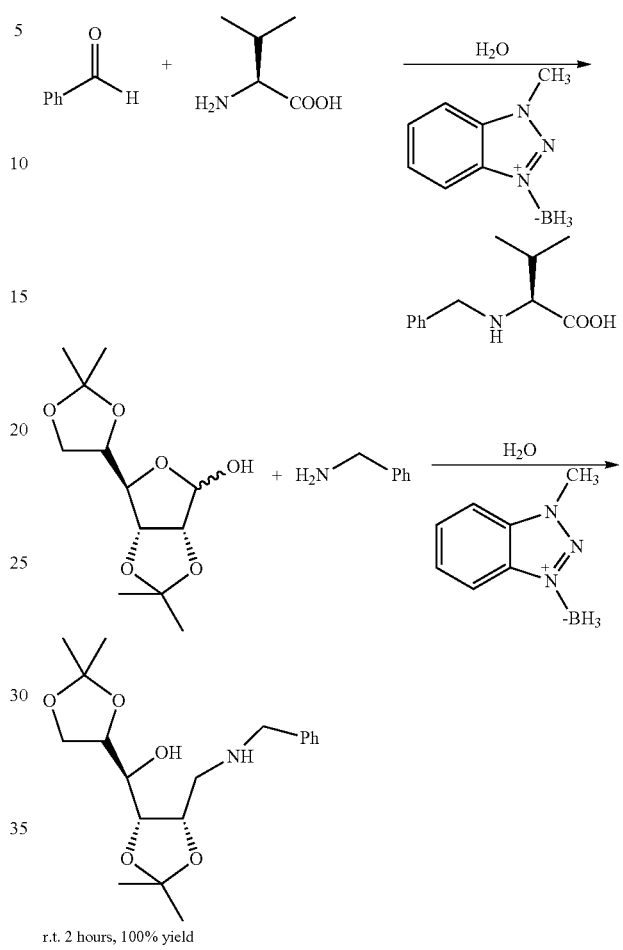

r.t. 2 hours, 100% yield

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

What is claimed is:

1. A compound of the formula

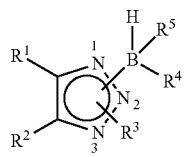

wherein $R^3$ can be attached to $N^1$, $N^2$, or $N^3$ and B can be attached to either of the other two remaining Ns and $R^1$, $R^2$, —$R^4$, and $R^5$ can be H, alkyl, aryl, substituted alkyl, or aryl groups and $R^3$ can be any alkyl, aryl, substituted alkyl, or aryl groups.

* * * * *